(12) United States Patent
Govari et al.

(10) Patent No.: US 8,847,587 B2
(45) Date of Patent: Sep. 30, 2014

(54) FIELD GENERATOR PATCH WITH DISTORTION CANCELLATION

(75) Inventors: Assaf Govari, Haifa (IL); Andres Claudio Altmann, Haifa (IL); Yaron Ephrath, Karkur (IL)

(73) Assignee: Biosense Webster (Israel) Ltd., Yokneam (IL)

(*) Notice: Subject to any disclaimer, the term of this patent is extended or adjusted under 35 U.S.C. 154(b) by 507 days.

(21) Appl. No.: 13/181,616

(22) Filed: Jul. 13, 2011

(65) Prior Publication Data

US 2013/0015848 A1    Jan. 17, 2013

(51) Int. Cl.
| | |
|---|---|
| G01N 27/72 | (2006.01) |
| G01R 33/12 | (2006.01) |
| A61B 19/00 | (2006.01) |
| H01F 5/00 | (2006.01) |
| A61B 17/00 | (2006.01) |

(52) U.S. Cl.
CPC ............ *A61B 19/5244* (2013.01); *H01F 5/003* (2013.01); *A61B 2019/5251* (2013.01); *A61B 2017/00725* (2013.01)
USPC ............ 324/228; 342/417; 342/418; 702/94; 702/150

(58) Field of Classification Search
USPC .................. 324/228, 318, 320; 342/417, 448; 702/94, 150
See application file for complete search history.

(56) References Cited

U.S. PATENT DOCUMENTS

| | | | |
|---|---|---|---|
| 4,890,061 A * | 12/1989 | Den Boef ..................... 324/320 |
| 5,391,199 A | 2/1995 | Ben-Haim |
| 5,773,976 A | 6/1998 | Sakakura et al. |
| 5,892,359 A * | 4/1999 | Yui et al. ..................... 324/318 |
| 6,111,409 A * | 8/2000 | Edwards et al. ............. 324/303 |
| 6,177,792 B1 | 1/2001 | Govari et al. |
| 6,239,724 B1 | 5/2001 | Doron et al. |
| 6,332,089 B1 | 12/2001 | Acker et al. |
| 6,366,799 B1 | 4/2002 | Acker et al. |
| 6,433,550 B1 * | 8/2002 | Kinanen ..................... 324/320 |
| 6,484,118 B1 | 11/2002 | Govari |
| 6,618,612 B1 | 9/2003 | Acker et al. |
| 6,690,963 B2 | 2/2004 | Ben-Haim et al. |
| 6,731,968 B2 | 5/2004 | Buchanan |

(Continued)

FOREIGN PATENT DOCUMENTS

| | | |
|---|---|---|
| EP | 1 178 327 A2 | 2/2002 |
| WO | WO 96/05768 A1 | 2/1996 |
| WO | WO 2010/114959 A1 | 10/2010 |

OTHER PUBLICATIONS

Extended European Search Report dated Oct. 25, 2012 received from related European Application No. 12176188.6.

*Primary Examiner* — Huy Q Phan
*Assistant Examiner* — Giovanni Astacio-Oquendo
(74) *Attorney, Agent, or Firm* — Louis J. Capezzuto

(57) ABSTRACT

A magnetic field generator includes a substrate, a main generator coil, at least one field sensor, at least one shim coil, a driver circuit and a correction circuit. The main generator coil, the field sensor, and the shim coil are all disposed on the substrate. The driver circuit is coupled to drive the main generator coil with a driving current at a selected frequency. The correction circuit is coupled to receive a signal at the selected frequency from the at least one field sensor and, in response to deviations in the signal from a predefined baseline, to drive the at least one shim coil with a driving current having an amplitude configured to return the signal to the baseline.

16 Claims, 2 Drawing Sheets

(56) References Cited

U.S. PATENT DOCUMENTS

| | | |
|---|---|---|
| 7,450,996 B2 | 11/2008 | MacDonald et al. |
| 2001/0010464 A1* | 8/2001 | Takamori et al. ............. 324/304 |
| 2002/0065455 A1 | 5/2002 | Ben-Haim et al. |
| 2003/0120150 A1 | 6/2003 | Govari |
| 2004/0068178 A1 | 4/2004 | Govari |
| 2005/0285597 A1* | 12/2005 | Maki et al. .................... 324/320 |
| 2009/0082989 A1 | 3/2009 | Zuhars et al. |
| 2009/0187096 A1* | 7/2009 | Tiernan et al. ................ 600/421 |
| 2009/0299175 A1 | 12/2009 | Bernstein et al. |
| 2010/0125194 A1* | 5/2010 | Bonner et al. ................ 600/424 |
| 2010/0211347 A1* | 8/2010 | Friedrich et al. ............. 702/117 |
| 2011/0137589 A1 | 6/2011 | Leskowitz et al. |
| 2012/0019946 A1* | 1/2012 | Aravind ........................ 360/39 |

\* cited by examiner

FIELD GENERATOR PATCH WITH DISTORTION CANCELLATION

FIELD OF THE INVENTION

The present invention relates generally to medical instruments, and particularly to methods and systems for position tracking of medical probes.

BACKGROUND OF THE INVENTION

Some magnetic position tracking systems track the position of a catheter or other probe in a patient's body by generating known magnetic fields and measuring the fields using a magnetic field sensor fitted in the probe. Systems of this sort are described, for example, in U.S. Pat. Nos. 5,391,199, 6,690,963, 6,484,118, 6,239,724, 6,618,612 and 6,332,089, PCT International Publication WO 96/05768, and U.S. Patent Application Publications 2002/0065455, 2003/0120150 and 2004/0068178, whose disclosures are all incorporated herein by reference.

U.S. Pat. No. 6,177,792, whose disclosure is incorporated herein by reference, describes an apparatus for generating magnetic fields, including a plurality of radiator coils and driver circuitry coupled thereto. The driver circuitry drives the coils so as to generate magnetic fields at a plurality of driving frequencies, wherein each of the plurality of radiator coils generates a field substantially only at a single, respective driving frequency. Circuitry is associated with at least one of the plurality of radiator coils for substantially eliminating magnetic fields generated by the other coils.

SUMMARY OF THE INVENTION

An embodiment of the present invention that is described hereinbelow provides a magnetic field generator including a substrate, a main generator coil, at least one field sensor, at least one shim coil, a driver circuit and a correction circuit. The main generator coil, the field sensor, and the shim coil are all disposed on the substrate. The driver circuit is coupled to drive the main generator coil with a driving current at a selected frequency. The correction circuit is coupled to receive a signal at the selected frequency from the at least one field sensor and, in response to deviations in the signal from a predefined baseline, to drive the at least one shim coil with a driving current having an amplitude configured to return the signal to the baseline.

In some embodiments, the substrate is flexible and is configured to be attached to a patient body. In an embodiment, the substrate includes a Printed Circuit Board (PCB), and the main generator coil, the at least one field sensor and the at least one shim coil include conductors that are printed on the PCB. In a disclosed embodiment, the at least one shim coil includes multiple shim coils, and the correction circuit is configured to generate, in response to the signal received from the field sensor, multiple respective driving currents for driving the shim coils.

In another embodiment, the multiple shim coils are disposed in different, mutually-spaced locations on the substrate. In an embodiment, the multiple shim coils include conductors that surround different, respective sub-areas of the substrate. In an example embodiment, the main coil surrounds an area of the substrate that contains the sub-areas of the shim coils.

In yet another embodiment, the correction circuit is coupled to detect the deviations from the predefined baseline, to estimate the driving current that cancels the deviations, and to drive the at least one shim coil with the estimated driving current. In still another embodiment, the correction circuit is coupled to estimate the baseline by measuring the signal produced by the at least one field sensor while the deviations are not present, and to generate the driving current by comparing the baseline to the signal produced by the at least one field sensor while the deviations are present.

There is additionally provided, in accordance with an embodiment of the present invention, a method including driving a main generator coil, which is disposed on a substrate, with a driving current at a selected frequency. A signal is received at the selected frequency from at least one sensing coil that is disposed on the substrate. In response to deviations in the signal from a predefined baseline, at least one shim coil, which is disposed on the substrate, is driven with a driving current having an amplitude configured to return the signal to the baseline.

The present invention will be more fully understood from the following detailed description of the embodiments thereof, taken together with the drawings in which:

DETAILED DESCRIPTION OF EMBODIMENTS

Overview

Some medical position tracking systems measure the position of an intra-body probe by generating a position-dependent magnetic field, and sensing the magnetic field at the probe. The magnetic field, which is referred to herein as a main magnetic field, is typically generated by one or more field generator coils having known positions. In practical operating environments, however, the main magnetic field may be distorted, for example by the presence of nearby metallic objects. This sort of distortion may cause erroneous position measurements.

Embodiments of the present invention that are described herein provide improved methods and systems for magnetic position tracking. The disclosed techniques correct the distortion in the main magnetic field of a given field generator coil using at least one field sensor and at least one shim coil that are mounted adjacently to the field generator coil. In some embodiments, the field sensor senses the main magnetic field and produces a signal that is indicative of the sensed field. A correction circuit uses this signal to generate a driving current for driving the shim coil. The driving current is generated so as to correct deviations of the main magnetic field from a predefined baseline.

Typically, the main magnetic field comprises an Alternating Current (AC) field. The correction circuit generates an AC correction current whose amplitude (including magnitude and phase) causes the shim coil to generate a correction magnetic field that returns the main magnetic field to the predefined baseline.

When the deviations are caused by metal disturbance, the correction magnetic field cancels this disturbance and prevents it from distorting the position measurements of the system. In an embodiment, the correction circuit operates in a real-time, adaptive manner and is therefore able to correct distortion that changes over time.

In some embodiments, the field generating coil, the field sensor and the shim coil are all disposed on a common substrate, such as on a flexible patch that is attached to the patient body. The close proximity of the patch elements, as well as their proximity to the tracked intra-body probe, enables highly accurate distortion correction. In some embodiments, the accuracy of the correction is further refined by using multiple shim coils and/or multiple sensing coils per field generator coil.

System Description

Figure 1:
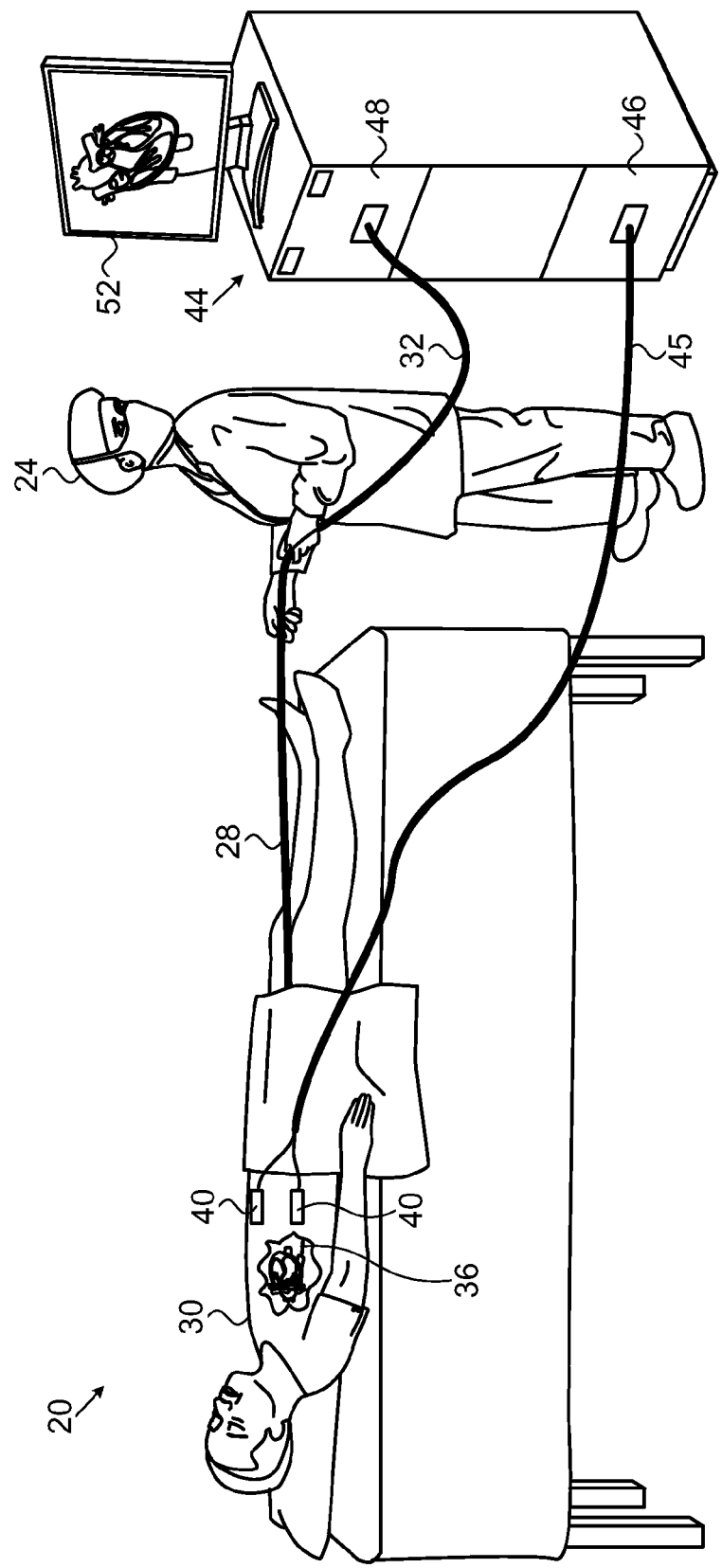
FIG. 1 is a schematic, pictorial illustration of a system for magnetic position tracking, in accordance with an embodiment of the present invention.

FIG. 1 is a schematic, pictorial illustration of a system 20 for cardiac catheterization that uses magnetic position tracking, in accordance with an embodiment of the present invention. System 20 may be based, for example, on the CARTO™ system, produced by Biosense-Webster Inc. (Diamond Bar, Calif.). In system 20, a physician 24 (or other operator) inserts a catheter 28 (or other probe) into the body of a patient 30.

Catheter 28 has a proximal end that is handled by the physician, and a distal end 36 that is navigated through the patient body. The physician moves the distal end of the catheter by manipulating the proximal end. Catheter 28 is connected to a control console 44 using a cable 32. In the embodiment described herein, catheter 28 is inserted into the patient's heart and used for ablation and/or for creating electrophysiological maps of one or more heart chambers. Alternatively, catheter 28 may be used, mutatis mutandis, for other therapeutic and/or diagnostic purposes in the heart or in other body organs.

Console 44 uses magnetic position sensing to determine position coordinates of distal end 36 inside the heart. For this purpose, patches 40 are attached to the body of patient 30. Although FIG. 1 shows two patches for the sake of clarity, in alternative embodiments system 20 may comprise any desired number of patches 40. Each patch 40 comprises a field generator coil (shown in detail in FIG. 2), as well as other elements that are described below. Patches 40 are connected by a cable 45 to a driver unit 46 in console 44.

Driver unit 46 drives the field generator coils in patches 40 to generate magnetic fields (referred to as main magnetic fields) within the body of patient 30. A magnetic position sensor (not shown in the figure) within distal end 36 of catheter 28 generates electrical signals in response to these magnetic fields. A processor 48 in console 44 processes these signals in order to determine the position coordinates of distal end 36, typically including both location and orientation coordinates. Magnetic position tracking methods of this sort are described in detail in U.S. Pat. Nos. 5,391,199, 6,690,963, 6,484,118, 6,239,724, 6,618,612 and 6,332,089, in PCT International Publication WO 96/05768, and in U.S. Patent Application Publications 2002/0065455, 2003/0120150 and 2004/0068178, cited above.

Based on the signals received from catheter 28, processor 44 drives a display 52 to present physician 24 with visual feedback regarding the position of distal end in the patient's body and status information and guidance regarding the procedure that is in progress.

The configuration of system 20 shown in FIG. 1 is an example configuration that is chosen purely for the sake of conceptual clarity. In alternative embodiments, any other suitable system configuration can be used. Processor 48 typically comprises a general-purpose computer, with suitable front end and interface circuits for receiving signals from catheter 28 and controlling the other components of console 44. Processor 48 may be programmed in software to carry out the functions that are described herein. The software may be downloaded to processor 48 in electronic form, over a network, for example, or it may be provided on non-transitory tangible media, such as optical, magnetic or electronic memory media. Alternatively, some or all of the functions of processor 48 may be carried out by dedicated or programmable digital hardware components.

Field Generator Patch with Distortion Cancellation

As explained above, the field generator coil in each patch 40 generates a main magnetic field in the body of patient 30. The position sensor in distal end 36 of catheter 28 senses these fields, and provides processor 48 with signals that are indicative of the position of the distal end relative to the patches.

In many practical scenarios, the main magnetic field is distorted, for example by nearby metallic objects. Unless accounted for, this distortion may cause processor to produce erroneous position measurements. In some embodiments, system 20 cancels out the distortion in the main magnetic field in an adaptive manner, as will be described below.

Figure 2:
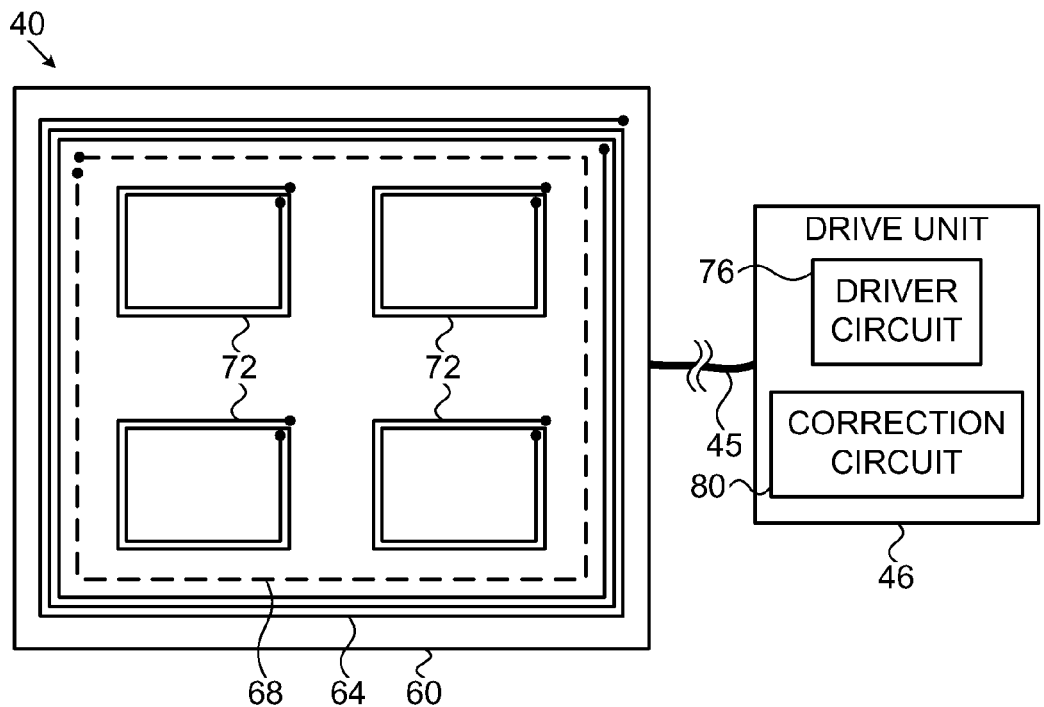
FIG. 2 is a block diagram that schematically illustrates elements of a system for magnetic position tracing, in accordance with an embodiment of the present invention.

FIG. 2 is a block diagram that schematically illustrates elements of system 20, in accordance with an embodiment of the present invention. The figure shows drive unit 46, which is connected by cable 45 to patch 40. Only a single patch 40 is shown in the figure for the sake of conceptual clarity. Typically, drive unit 46 is connected by cable 45 to multiple patches 40 of this sort.

Patch 40 comprises a substrate 60, which is typically flexible in order to conform to the shape of the patient body when attached. The patch may be attached to the body using any suitable means, such as using an adhesive material or tape. Several coils are disposed on substrate 60, in the present example a field generating coil 64, a field sensing coil 68 and four shim coils 72. Drive unit 46 comprises a driver circuit 76 and a correction circuit 80.

Driver circuit 76 drives field generating coil 64 with AC driving current at a selected frequency. The driving current causes coil 64 to generate a main magnetic field. Sensing coil 68 senses the main magnetic field in the vicinity of coil 64 and produces a respective signal, which has the frequency of the main magnetic field. When the main magnetic field is not distorted (e.g., when no metallic objects are nearby), the magnetic field sensed by coil 68 will typically comply with a predefined baseline. When the main magnetic field is distorted, the magnetic field sensed by coil 68 will typically deviate from the baseline.

Correction circuit 80 in unit 46 receives the signal from sensing coil 68. This signal typically has the same frequency as that of the main magnetic field. Using the signal received from sensing coil 68, correction circuit 80 identifies deviations of the main magnetic field from the predefined baseline. The correction circuit generates one or more correction currents, which compensate for these deviations, and drives shim coils 72 with the correction currents.

The amplitudes of the correction currents are set by circuit 80 so as to cause the shim coils to generate correction magnetic fields that cancel out the distortion of the magnetic field. In other words, the correction magnetic fields generated by shim coils 72 return the main magnetic field to the predefined base line. As a result of this correction, the net magnetic field generated by patch 40 complies with the predefined baseline.

In the context of the present patent application and in the claims, the term "amplitude" is used broadly to refer to the complex amplitude of an AC signal, including both phase and magnitude components.

Correction circuit 80 may detect and correct deviations in the main magnetic field in any suitable way. In an example embodiment, the correction circuit estimates the baseline by initially operating field generator coil 64 in a controlled environment, without elements that could distort the main magnetic field. Under these conditions, sensor coil 68 senses the magnetic field, and the sensing coil signal is regarded as the baseline. During normal operation, while the deviations may be present, correction circuit 80 generates the driving current for the shim coils by comparing the baseline to the sensing coil signal. In an embodiment, the correction circuit searches for a combination of correction currents that, when driving shim coils 72, will cancel-out deviations from the baseline field. The search may be performed, for example, using analog or digital feedback that is based on the difference between the signal of sensing coil 68 and the baseline, by a greedy or exhaustive search process that attempts to zero this difference, or using any other suitable scheme.

Typically, correction circuit 80 carries out the above-described correction process continually or periodically, in an adaptive manner. In other words, the correction circuit receives, continually or periodically, a signal from sensing coil 68, and drives shim coils 72 with appropriate correction currents. Thus, system 20 is able to correct time-varying distortions in the main magnetic field. Such time-varying distortion may be caused, for example, by moving objects such as surgical tools or other equipment.

In some embodiments, substrate 60 comprises a flexible Printed Circuit Board (PCB) material, and coils 64, 68 and 72 are disposed using PCB conductors. In the example of FIG. 2, field generator coil 64 and shim coils 72 are disposed on one side of substrate 60, and sense coil 68 is disposed on the opposite side of the substrate. This configuration, however, is chosen purely for the sake of conceptual clarity. In alternative embodiments, any other suitable configuration can be used.

For example, substrate 60 may be rigid and not necessarily flexible. In some embodiments, the elements of patch 40 may not be attached to the patient body, but rather rigidly fixed at known locations relative to one another. In some embodiments, the main magnetic field may be sensed by any other suitable kind of field sensor, not necessarily a sensing coil.

In the example of FIG. 2, multiple shim coils 72 are disposed in different, mutually-spaced locations on substrate 60. The multiple shim coils comprise conductors that surround different, respective sub-areas of the substrate, and field generator coil 64 surrounds an area of substrate 60 that contains the sub-areas of the shim coils. Alternatively, however, any other suitable configuration can be used.

Although the present example shows a single field generator coil, a single sensing coil and four shim coils, in alternative embodiments patch 40 may comprise any other suitable number of field generator coils, field sensors and shim coils. In an example embodiment patch 40 comprises a single shim coil. In another example embodiment, patch 40 may comprise multiple field sensors (e.g., sensing coils), one per each shim coil. In this embodiment, correction circuit drives each shim coil with a respective correction current that is generated based on the field sensed by the corresponding sensing coil.

Correction circuit 80 may be implemented using analog circuitry, using digital circuitry, or both. In some embodiments, the functions of correction circuit 80 may be implemented in software, for example as part of processor 48.

Distortion Cancellation Method Description

Figure 3:
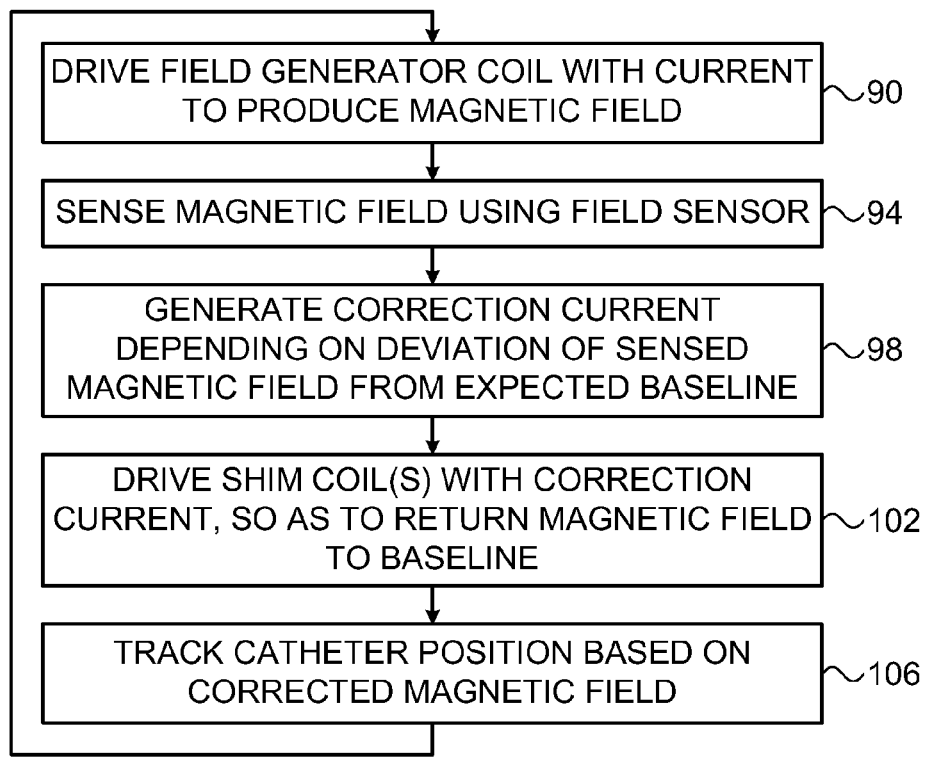
FIG. 3 is a flow chart that schematically illustrates a method for correcting field distortion in a magnetic position tracking system, in accordance with an embodiment of the present invention.

FIG. 3 is a flow chart that schematically illustrates a method for correcting field distortion in system 20, in accordance with an embodiment of the present invention. The following description refers to a single patch 40 having a single field generator coil, a single sensing coil and a single shim coil. The method, however, can be applied in a similar manner, in other patch configurations.

The method begins with driver circuit 76 driving field generator coil 64 of patch 40 with driving current at a selected frequency, at a main driving step 90. In response to this driving current, field generating coil generates a main magnetic field at the selected frequency.

Sensing coil 68 of patch 40 senses the main magnetic field, at a sensing step 94, and produces a corresponding signal at the selected frequency. Correction circuit 80 receives the signal from sensing coil 68, and uses the signal to generate a correction current, at a correction current generation step 98. The correction current depends on the deviation of the main magnetic field, as sensed by coil 68, from its predefined baseline. The correction current is configured, when driving shim coil 72, to return the main magnetic field to the predefined baseline. In other words, the correction current is configured to compensate for the deviation in the main magnetic field.

Correction circuit 80 drives shim coil 72 with the correction current, at a correction driving step 102. As a result, the shim coil generates a correction magnetic field that compensates for the distortion in the main magnetic field. System 20 tracks the position of catheter 28 in the body of patient 30 using the corrected magnetic field, at a position tracking step 106. Since the position measurements of system 20 are based on the corrected magnetic field, they are unaffected by the distortion of the main magnetic field, and therefore accurate.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A magnetic field generator, comprising:
   a substrate;
   a main generator coil, at least one field sensor, and at least one shim coil, all disposed on the substrate;
   a driver circuit, which is coupled to drive the main generator coil with a driving current at a selected frequency; and
   a correction circuit, which is coupled to receive a signal at the selected frequency from the at least one field sensor and, in response to deviations in the signal from a predefined baseline, to drive the at least one shim coil with a driving current having an amplitude configured to return the signal to the baseline, the correction circuit being coupled to detect the deviations from the predefined baseline, to estimate the driving current that cancels the deviations, and to drive the at least one shim coil with the estimated driving current.

2. The field generator according to claim 1, wherein the substrate is flexible and is configured to be attached to a patient body.

3. The field generator according to claim 1, wherein the substrate comprises a Printed Circuit Board (PCB), and wherein the main generator coil, the at least one field sensor and the at least one shim coil comprise conductors that are printed on the PCB.

4. The field generator according to claim 1, wherein the at least one shim coil comprises multiple shim coils, and wherein the correction circuit is configured to generate, in response to the signal received from the field sensor, multiple respective driving currents for driving the shim coils.

5. The field generator according to claim 4, wherein the multiple shim coils are disposed in different, mutually-spaced locations on the substrate.

6. The field generator according to claim 5, wherein the multiple shim coils comprise conductors that surround different, respective sub-areas of the substrate.

7. The field generator according to claim 6, wherein the main coil surrounds an area of the substrate that contains the sub-areas of the shim coils.

8. The field generator according to claim 1, wherein the correction circuit is coupled to estimate the baseline by measuring the signal produced by the at least one field sensor while the deviations are not present, and to generate the driving current by comparing the baseline to the signal produced by the at least one field sensor while the deviations are present.

9. A method, comprising:
   driving a main generator coil, which is disposed on a substrate, with a driving current at a selected frequency;
   receiving a signal at the selected frequency from at least one sensing coil that is disposed on the substrate; and
   in response to deviations in the signal from a predefined baseline, driving at least one shim coil, which is disposed on the substrate, with a driving current having an amplitude configured to return the signal to the baseline,
   wherein driving the at least one shim coil comprises detecting the deviations from the redefined baseline, estimating the driving current that cancels the deviations, and driving the at least one shim coil with the estimated driving current.

10. The method according to claim 9, wherein the substrate is flexible and is configured to be attached to a patient body.

11. The method according to claim 9, wherein the substrate comprises a Printed Circuit Board (PCB), and wherein the main generator coil, the at least one field sensor and the at least one shim coil comprise conductors that are printed on the PCB.

12. The method according to claim 9, wherein the at least one shim coil comprises multiple shim coils, and wherein driving the at least one shim coil comprises generating, in response to the signal received from the field sensor, multiple respective driving currents for driving the shim coils.

13. The method according to claim 12, wherein the multiple shim coils are disposed in different, mutually-spaced locations on the substrate.

14. The method according to claim 13, wherein the multiple shim coils comprise conductors that surround different, respective sub-areas of the substrate.

15. The method according to claim 14, wherein the main coil surrounds an area of the substrate that contains the sub-areas of the shim coils.

16. The method according to claim 9, wherein driving the at least one shim coil comprises estimating the baseline by measuring the signal produced by the at least one field sensor while the deviations are not present, and generating the driving current by comparing the baseline to the signal produced by the at least one field sensor while the deviations are present.

* * * * *